(12) United States Patent
Okuma

(10) Patent No.: US 9,844,652 B2
(45) Date of Patent: Dec. 19, 2017

(54) STENT KIT

(71) Applicant: Gadelius Medical, K. K., Tokyo (JP)

(72) Inventor: Nobuaki Okuma, Tokyo (JP)

(73) Assignee: Gadelius Medical, K.K., Tokyo (JP)

( * ) Notice: Subject to any disclaimer, the term of this patent is extended or adjusted under 35 U.S.C. 154(b) by 729 days.

(21) Appl. No.: 14/310,019

(22) Filed: Jun. 20, 2014

(65) Prior Publication Data

US 2015/0005864 A1  Jan. 1, 2015

(30) Foreign Application Priority Data

Jun. 28, 2013 (JP) ................................. 2013-135891

(51) Int. Cl.
*A61F 2/06* (2013.01)
*A61M 27/00* (2006.01)

(52) U.S. Cl.
CPC ................................. *A61M 27/008* (2013.01)

(58) Field of Classification Search
CPC .................................................. A61M 27/008
See application file for complete search history.

(56) References Cited

U.S. PATENT DOCUMENTS

| 4,643,716 | A | * | 2/1987 | Drach | A61M 27/008 604/544 |
|---|---|---|---|---|---|
| 4,790,809 | A | * | 12/1988 | Kuntz | A61M 25/0045 600/434 |
| 4,790,810 | A | * | 12/1988 | Pugh, Jr. | A61F 2/94 604/544 |
| 4,931,037 | A | * | 6/1990 | Wetterman | A61M 27/008 604/544 |
| 5,052,998 | A | * | 10/1991 | Zimmon | A61F 2/94 604/530 |
| 5,599,291 | A | * | 2/1997 | Balbierz | A61L 27/34 604/264 |
| 5,681,274 | A | * | 10/1997 | Perkins | A61M 25/00 604/264 |
| 5,921,952 | A | * | 7/1999 | Desmond, III | A61M 27/008 604/8 |
| 6,248,100 | B1 | * | 6/2001 | de Toledo | A61M 25/01 604/500 |
| 6,264,624 | B1 | | 7/2001 | Desmond, III et al. | |
| 6,929,664 | B2 | * | 8/2005 | Kolb | A61F 2/04 264/211.12 |
| 7,550,012 | B2 | * | 6/2009 | Lavelle | A61M 27/008 604/8 |
| 8,034,094 | B2 | * | 10/2011 | Aoba | A61F 2/94 623/1.11 |
| 8,657,884 | B2 | * | 2/2014 | Smouse | A61M 27/008 604/8 |

(Continued)

FOREIGN PATENT DOCUMENTS

WO  2008-115271 A2  9/2008

*Primary Examiner* — Son Dang

(74) *Attorney, Agent, or Firm* — Howson & Howson LLP

(57) ABSTRACT

In a stent kit in which a stent tube has an arc-shaped part at one or both ends, an inner catheter includes an arc-shaped part fitting in, and conforming to, each arc-shaped part of the stent tube. Because of the conforming shapes, the stent tube is not deformed by the inner catheter even if the inner catheter remains within the stent tube over a long time. Consequently, the arcuate shape of the arc-shaped part or parts of the stent tube are reliably restored when the inner catheter is pulled out.

8 Claims, 4 Drawing Sheets

(56) References Cited

U.S. PATENT DOCUMENTS

| | | | | |
|---|---|---|---|---|
| 8,696,732 B2* | 4/2014 | Leanna | A61F 2/94 623/1.11 |
| 8,753,303 B2* | 6/2014 | Weisman | A61F 2/95 604/8 |
| 8,808,348 B2* | 8/2014 | Hollett | A61F 2/94 623/1.11 |
| 8,961,581 B2* | 2/2015 | Hollett | A61F 2/95 623/1.11 |
| 9,333,063 B2* | 5/2016 | Li | A61F 2/0045 |
| 9,649,213 B2* | 5/2017 | Hollett | A61F 2/94 |
| 2004/0087886 A1* | 5/2004 | Gellman | A61F 2/88 604/8 |
| 2004/0181186 A1* | 9/2004 | Gellman | A61M 27/008 604/8 |
| 2005/0085891 A1* | 4/2005 | Goto | A61F 2/94 623/1.11 |
| 2005/0085892 A1* | 4/2005 | Goto | A61F 2/94 623/1.12 |
| 2005/0240278 A1* | 10/2005 | Aliski | A61F 2/04 623/23.7 |
| 2006/0253104 A1* | 11/2006 | Pandey | A61M 27/008 604/540 |
| 2006/0276873 A1* | 12/2006 | Sato | A61B 17/3468 623/1.11 |
| 2007/0276466 A1* | 11/2007 | Lavelle | A61F 2/04 623/1.22 |
| 2007/0293929 A1* | 12/2007 | Aoba | A61F 2/95 623/1.11 |
| 2008/0004578 A1* | 1/2008 | Hixon | A61L 31/148 604/326 |
| 2008/0004685 A1* | 1/2008 | Seemann | A61F 2/95 623/1.11 |
| 2008/0051911 A1* | 2/2008 | Rucker | A61F 2/04 623/23.7 |
| 2008/0086215 A1* | 4/2008 | St. Pierre | A61M 25/0009 623/23.66 |
| 2008/0183299 A1* | 7/2008 | Monga | A61F 2/04 623/23.66 |
| 2009/0143849 A1* | 6/2009 | Ozawa | A61F 2/94 623/1.11 |
| 2012/0095545 A1* | 4/2012 | Yamagata | A61F 2/82 623/1.16 |
| 2012/0095566 A1* | 4/2012 | Teague | A61F 2/04 623/23.7 |
| 2012/0303109 A1* | 11/2012 | Okuma | A61F 2/95 623/1.11 |
| 2013/0060238 A1* | 3/2013 | Lavelle | A61F 2/88 604/544 |
| 2013/0158673 A1* | 6/2013 | Toomey | A61F 2/04 623/23.7 |
| 2014/0188249 A1* | 7/2014 | Pendleton | A61M 27/008 623/23.66 |
| 2015/0005893 A1* | 1/2015 | Harrah | A61L 31/148 623/23.7 |
| 2015/0134073 A1* | 5/2015 | Tang | A61M 27/008 623/23.7 |
| 2015/0142127 A1* | 5/2015 | Ponsky | A61M 27/008 623/23.69 |
| 2015/0343187 A1* | 12/2015 | Vogt | A61F 2/82 623/23.65 |
| 2016/0015509 A1* | 1/2016 | McDonough | A61F 2/88 623/23.7 |
| 2016/0045347 A1* | 2/2016 | Smouse | A61F 2/95 623/23.66 |
| 2016/0113787 A1* | 4/2016 | Biltz | A61F 2/94 623/23.7 |
| 2016/0199170 A1* | 7/2016 | Biltz | A61M 27/008 623/23.66 |

* cited by examiner

STENT KIT

FIELD OF THE INVENTION

This invention relates to stent kits, which are made and supplied as products in a condition in which an inner catheter is inserted into a stent tube. The stent tube can be made from any of a variety of materials, usually a plastics material such as polyethylene. In this invention, the stent tube, which is hereinafter sometimes also referred to as a "stent", is a pig-tail shaped stent.

BACKGROUND OF THE INVENTION

There are many variations of stent tubes made from plastics such as polyethylene and other materials. Some have side holes or flaps and others do not. Some are straight, while others are curved, or have a pig-tail shape. These stent tubes are pushed forward, for placement within ducts or vessels in human bodies, by pusher catheters, along guide wires or along inner catheters, which are inserted into the human body. Systems have been developed for pulling back stents when the stents are pushed too far forward relative to the intended indwelling positions.

U.S. Pat. No. 6,264,624 discloses a delivery system having coupling means which ensures a connected condition between a stent and a pusher catheter. An end of a loop of a filament provided on the pusher catheter is inserted into a flap of the stent, and an inner catheter is inserted into the end of the loop.

U.S. Pat. No. 8,034,094 also discloses a delivery system having coupling means which ensures a connected condition between a stent and a pusher catheter. A loop of filament is connected to a pusher catheter, and threaded into a hole provided on the stent. Thereafter the loop is inserting into the pusher catheter, and locked by a locking member which is formed separately from the inner catheter. The connection is released by pulling the filament by the locking member or by a separate pulling member after the inner catheter is pulled out.

United States Patent Publication 2013/0303109 discloses a delivery system having coupling means, wherein a filament having a knot is tied to a radial hole formed in a pusher catheter. An inner catheter is inserted into the pusher catheter and the stent while the knot fits loosely in a catching hole in the wall of the stent. A distal end of the filament extends beyond the catching hole when viewed from the side of the pusher catheter.

SUMMARY OF THE INVENTION

The delivery systems disclosed in the above-mentioned patents and patent publication are usually provided to the users as assembled products. Specifically, the coupling means between the stent and the pusher catheters is assembled and the inner catheter is inserted into the stent and the pusher catheter.

As shown FIG. 2, however, the so-called "pig-tail" stent, which has an arc-shaped part formed at least at one of its ends, has not been supplied as a product having an inner catheter inserted into the stent. Therefore, it has not been supplied in a condition in which a coupling between the stent and a pusher catheter is assembled. The reason is that a pig-tail shaped stent needs to restore its characteristic shape, with one or two circular, arc-shaped parts, when the stent is in an indwelled condition within a human body. The ends of the stent are unable to return to their circular arcuate shape when the inner catheter remains inserted in the stent for a long time.

It is also troublesome for a physician to insert an inner catheter into a pig-tail stent in order to use the stent. Furthermore, a pig-tail stent cannot be pulled back in the way in which the straight stents in the above-mentioned United States patents and patent publication are pulled back. Thus, pig-tail stents are not able to be pulled back when they are pushed by pusher catheters beyond their intended indwelling positions. If a pig-tail stent is pushed too far, It has been necessary to remove it and insert it again, which is time-consuming and inconvenient.

Accordingly, an object of the invention is to address the above problems by providing a stent kit having a pig-tail shaped stent which can be restored reliably to its pig-tail shape, and to provide a stent kit in which the stent can be pulled back if inserted too far.

The invention solves the above problems by a stent kit which, as supplied prior to the commencement of surgical implantation, comprises a plastic, pig-tail shaped stent tube and a removable inner catheter. The stent tube has a longitudinal centerline and first and second ends. At least at one of it's the ends of the stent tube, the longitudinal centerline is in the form of an arc subtending an angle of at least 45 degrees. Thus the relaxed shape of the part of the stent tube at that end of the stent tube is in the shape of a loop or partial loop. The inner catheter fits into the stent tube and has a part having the same shape as, and fitting within, the part of the stent tube in the shape of a loop or partial loop. Thus, the inner catheter does not tend exert a significant force tending to deform the stent tube by uncoiling the loop or partial loop. The inner catheter and stent tube are arranged such that the inner catheter can be pulled out of the stent tube.

In the stent kit according to the invention, because the arc-shaped part or parts of the inner catheter have the same shape as the arc-shaped parts of the stent in which they are situated, the arc-shaped part or parts of the stent are not deformed by the inner catheter even if the inner catheter remains inside the stent for a long time. Thus, the shape of the arc-shaped part or parts is reliably restored when the inner catheter is pulled out. The need to insert the inner catheter into the stent immediately before placement of the stent, which is especially troublesome in the case of a double pig-tail shaped stent having arc-shaped parts at both ends, is avoided.

The stent kit according to the invention can further comprise a pusher catheter located adjacent to and aligned with one of the ends of said stent tube. The inner catheter can extend from within the pusher catheter into the stent tube, and coupling means can be provided for coupling the stent tube to the pusher catheter so that the pig-tail shaped stent can be pulled back if necessary.

The stent kit can also comprising a straight cylindrical member in which the stent tube is inserted to maintain the stent in a straight condition so that a guide wire can be readily inserted into the inner catheter.

DETAILED DESCRIPTION OF THE PREFERRED EMBODIMENT

Several embodiments of the invention are described below with reference to FIGS. 1-5. The invention, however, is not limited to those embodiments.

Figure 1:
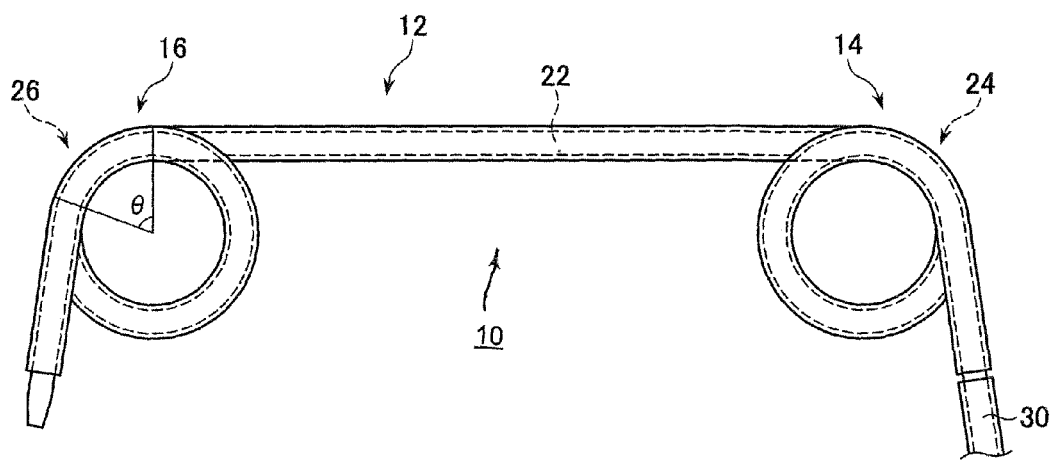
FIG. 1 is a side elevational view showing the principal components of a stent kit according to a first embodiment of the invention.
Figure 2A:
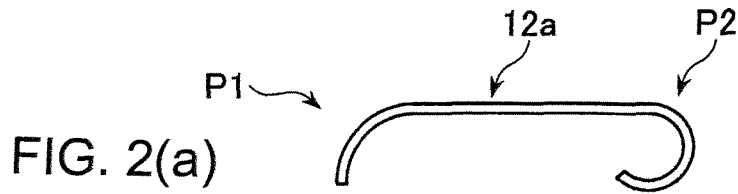
FIGS. 2(*a*)-2(*g*) show a variety of pig-tail shaped stents.
Figure 2B:
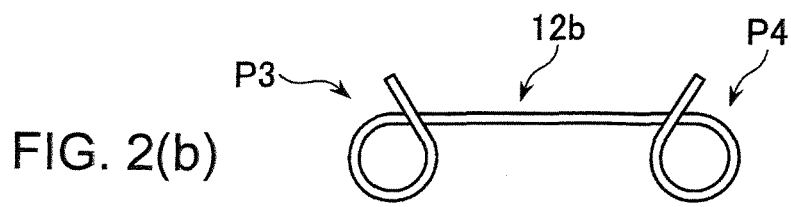
Figure 2C:
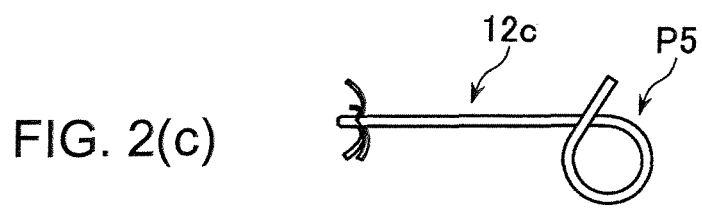
Figure 2D:
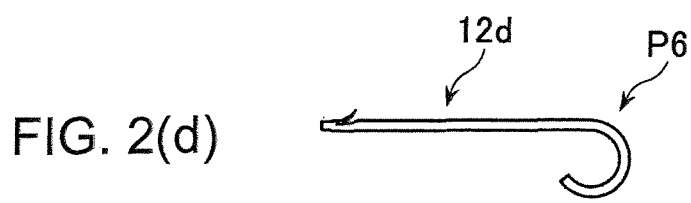
Figure 2E:
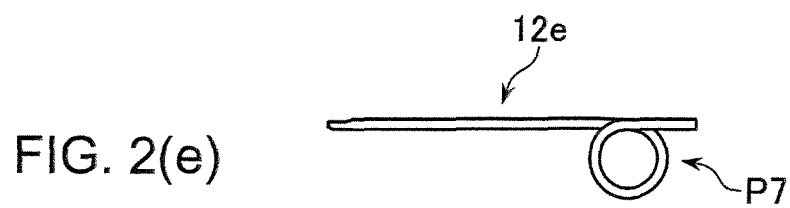
Figure 2F:
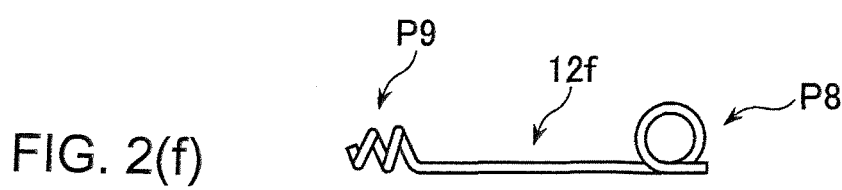
Figure 2G:
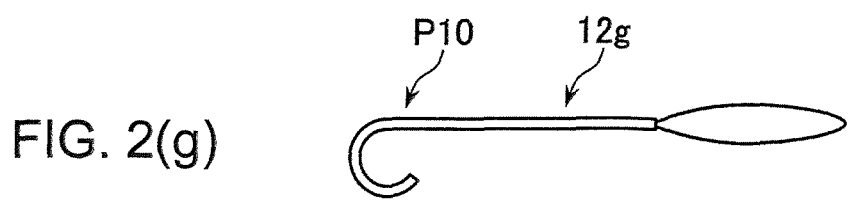

As shown in FIG. 1, a stent kit 10 comprises a stent tube 12, a removable inner catheter 22, and a pusher catheter 30. A first arc-shaped part 14 and a second arc-shaped part 16 are formed at the respective ends of the stent tube 12. In each of these parts, the longitudinal centerline of the stent tube is in the form of an arc. Stent tube 12 is a pig-tail shaped stent in which the arc-shaped parts 14 and 16 are in the form of loops in each of which the longitudinal centerline of the stent tube subtends an angle of approximately 430 degrees so that each loop has an overlapping part extending through an angle of approximately 70 degrees. Similar arc-shaped part 24 and 26 are formed in the inner catheter 22, and the longitudinal centerline in each of these arc-shaped parts of the inner catheter also subtends an angle of 430 degrees, so that the arc-shaped parts 24 and 26 of the inner catheter fit the arc-shaped parts 14 and 16 of the stent tube without exerting a significant force tending to uncoil the arc-shaped parts of the stent tube. The arc-shaped parts of the stent tube 12 and the inner catheter 22 can be formed by various processes such as thermoforming.

As shown in the FIG. 1, because the arc-shaped parts 24 and 26 of the inner catheter 22 fit the arc-shaped parts 14 and 16 of the stent tube 12 in the stent kit as supplied, the arc-shaped parts are not deformed by the inner catheter 22 even if the inner catheter remains inside the stent tube for a long time prior to surgical implantation. The arcuate shapes of the ends of the stent tube 12 are able to be restored positively when the inner catheter 22 is pulled out after placement of the stent. Accordingly, even a pig-tail shaped stent can be provided as a stent kit, with the inner catheter already inserted into the stent, and the difficulty of inserting the inner catheter into the stent immediately before placement can be avoided. Further, as shown in FIG. 1, the stent kit can be supplied with the inner catheter already inserted through a pusher catheter 30 axially aligned with one end of the stent tube. Consequently, the inconvenience of inserting the inner catheter 22 into the pusher catheter 30 immediately before stent placement can be avoided.

In using the stent kit 10, both ends of the stent tube 12 are pulled and the inner catheter 22 is also pulled so that the stent tube and inner catheter become approximately straight. Then, a guide wire (not shown in FIG. 1) is inserted through the inner catheter 22. The stent tube 12 and the inner catheter 22 are held approximately straight while the guide wire is inserted because, although the guide wire is made from a material having some flexibility, it is not as easily bent as the stent tube and inner catheter. Following passage of the guide wire through the inner catheter, the guide wire is inserted into a human body. Then the stent tube 12 is pushed along with the inner catheter 22 along the guide wire by the pusher catheter 30. When the stent reaches the intended indwelling position, the inner catheter 22, the pusher catheter 30, and the guide wire, are pulled out to complete the placement of the stent 12. In the process of placement of the stent the stent tube 12 is held straight temporarily, but the time during which it is in a straight condition is not so long as to cause a permanent change in the relaxed shape of the stent. The shapes of arc-shaped parts of the stent tube 12 are restored when the placement of the stent is completed.

Because the inner catheter 22 is formed with arc-shaped parts 24 and 26, the tendency of the inner catheter to curl results in some frictional resistance due to rubbing as it is pulled out of the stent tube. This frictional resistance is relatively large compared with that of the traditional inner catheter, which is not formed with arc-shaped parts. Accordingly, it is preferable that the stent 12 and the inner catheter 22 be made from materials such as polyethylene (PE) for the stent tube, and ethylene-tetrafluoroethylene copolymer (ETFE) for the inner catheter, so that the inner catheter 22 can slide easily relative to the stent tube 12, as it is pulled out from the stent tube.

FIGS. 2(a)-2(g) show typical examples of pig-tail shaped stents for which the invention is applicable. In these stents, the length of each arc-shaped part is about one-third the length of the stent tube. Some of the stents 12a-12g have similar arc-shaped parts but different overall shapes.

Preferably, the invention is applied to a stent in which the angle subtended by the arc-shaped part is 45 degrees or more. Thus, the invention is applicable to the stent tube 12a in FIG. 2(a), in which one of the arc-shaped parts, P1, subtends an angle of approximately 90 degrees. In this case, the inner catheter (not shown in FIG. 2(a)) will be formed in the same shape. Although the invention can be applied to stents in which the arc-shaped parts subtend less than 45 degrees, in such cases, restoration of the shape of stent is not much different from restoration when a straight inner catheter is used. As shown in FIGS. 2(a)-2(g), the invention can be applied not only to stents that have loops or partial loops at one or both ends that extend around axes transverse to the lengthwise dimensions of the stents, but also to stents such as stent 12f in FIG. 2(f), where the arc-shaped part P9 is in the form of a helix having its axis extending in a direction parallel to the lengthwise dimension of the stent.

Figure 3:
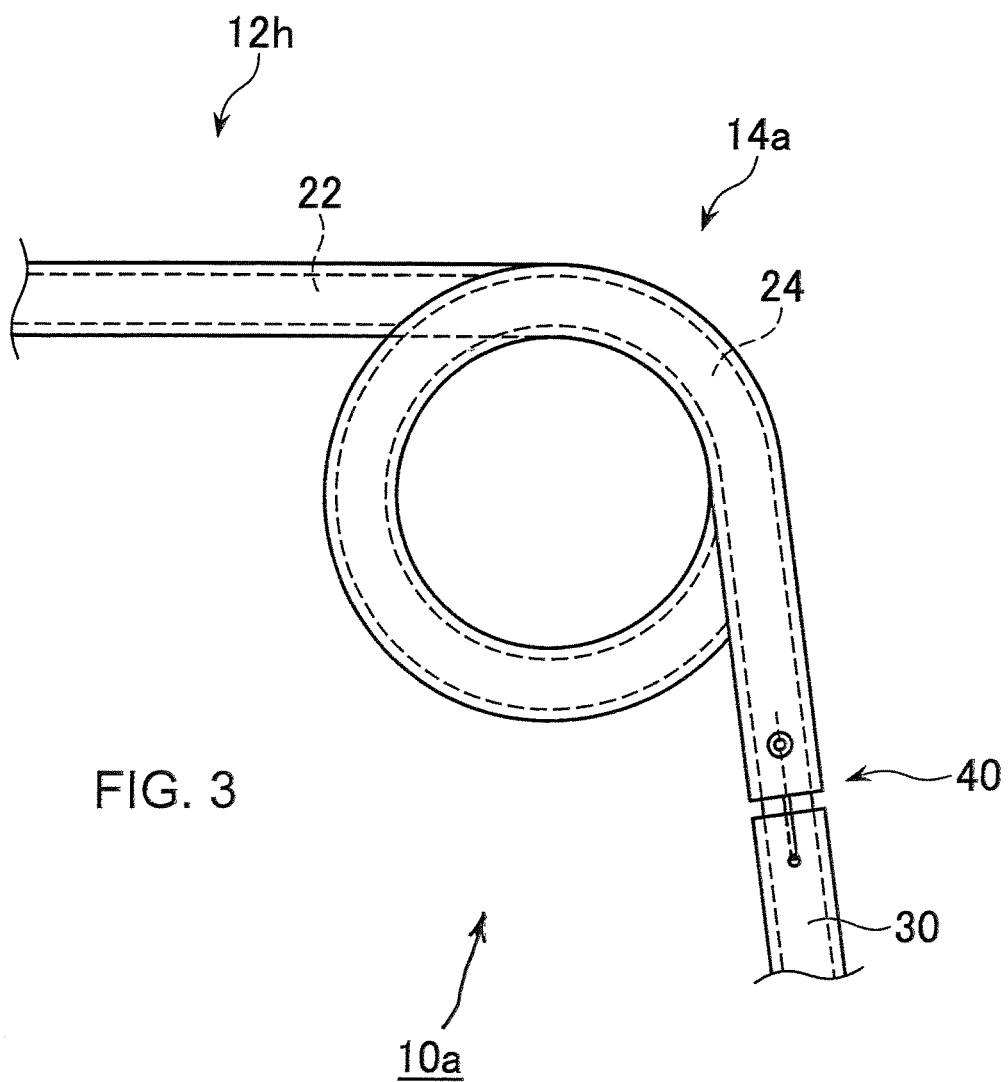
FIG. 3 is a side elevational view of a part of a stent kit according to a second embodiment of the invention, illustrating a coupling between a stent tube and a pusher catheter.

The stent kit 10a as shown in FIG. 3 comprises a pig-tail shaped stent tube 12h, an inner catheter 22, and a pusher catheter 30. This stent kit further comprises a coupling means 40 between the stent tube 12h and the pusher catheter 30. In the stent kit 10a, the inner catheter 22 is inserted into the stent tube 12h, and the first inner arc-shaped part 24 of the inner catheter 22 fits within the first arc-shaped part 14a of the stent tube.

Figure 4:
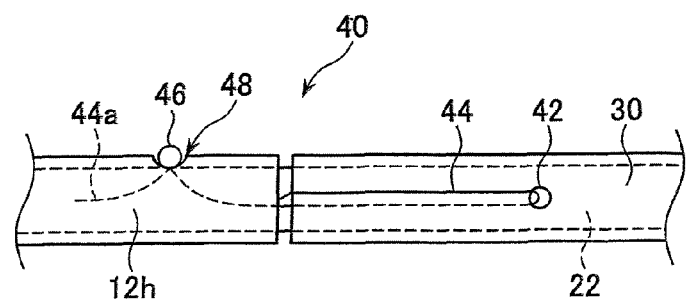
FIG. 4 is a side elevational view illustrating the coupling means in greater detail.

A coupling means 40, for connecting the stent tube to the pusher catheter, can be the same as the coupling means described in United States Patent Publication 2013/0303109. As shown in FIG. 4, the coupling means 40 has a knot 46 tied in a filament 44 that extends through a radial opening 42 formed in the wall of the pusher catheter 30. A catching hole 48 is formed in the wall of the stent tube 12h. The filament 44 and the knot 46 are inserted into the stent tube 12h, the inner catheter 22 is inserted through the pusher catheter 30, and the stent tube 12h in such a way that the knot 46 fits loosely in the catching hole 48, and is supported by the inner catheter 22, which prevents the knot from being released and moving inward through the catching hole into the interior of the stent tube. If the pusher catheter 30 is pulled, the stent 12 can be pulled back because the knot 46 is caught by the catching hole 48. However, when the stent is in its desired indwelling position, the inner catheter 22 can be pulled out of the stent tube 12h, releasing the knot 46 from the catching hole 48, and allowing the knot 46 to move into the inside of the stent. The pusher catheter 30 can then be pulled away from the stent, leaving the stent in its indwelling position.

The catching hole 48 is preferably positioned near the proximal end of the stent tube 12h so that the knot 46 can be pulled out instantly from the stent. An end 44a of the filament 44 preferably extends beyond the catching hole 48 and between the stent tube 12h and the inner catheter 22, when viewed from the side as in FIG. 4. The end 4a assists in preventing the knot 46 from being completely pushed outward the catching hole 48, and consequently the knot 46 moves easily to the inside of the stent tube 12h when the inner catheter 22 is pulled out.

From the foregoing, it can be appreciated that the invention allows a pig-tail shaped stent and a coupling means to be provided in a preassembled condition and the assembly can include the pusher catheter. Although the coupling means comprising a knotted filament, a catching hole and an inner catheter are shown, various other kinds of couplings can be utilized to connect the stent tube to the pusher catheter to allow the stent tube to be pulled back when necessary.

Figure 5:
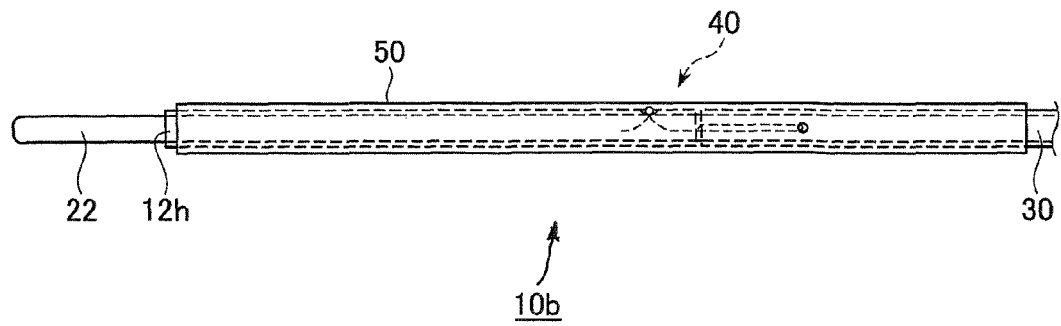
FIG. 5 is a side elevational view of a third embodiment of the stent kit of the invention, illustrating the use of an external cylindrical member to maintain the stent tube in a straight condition.

A stent kit 10b, shown in FIG. 5, has the same configuration as the stent kit 10a of FIG. 3, but includes a straightener 50 which is in the form of a straight, hollow, cylindrical member. By inserting the inner catheter 22 and the stent tube 12h into the straightener 50 the inner catheter 22 and the stent 12h can be kept in a straight condition, i.e., without the arc-shaped parts curling, so that a guide wire (not shown) can be inserted easily through the inside of the inner catheter 22.

In summary, the invention provides a preassembled stent kit in which an inner catheter is inserted into a pig-tail shaped stent, and has the advantageous feature that it enables the pigtail stent to be pulled back when necessary in the process of stent placement.

What is claimed is:

1. A stent kit comprising, as supplied prior to the commencement of surgical implantation:
   a plastic, pig-tail shaped stent tube having first and second ends and a longitudinal centerline, said stent tube being formed so that, in a part of said stent tube at least at one of said ends, said centerline is in the form of an arc and the relaxed shape of said part is in the form of a loop or a partial loop, and wherein the angle subtended by said arc is at least 45 degrees; and
   an inner catheter fitted into said stent tube, said inner catheter having a part fitting within said part of said stent tube, said part of the inner catheter being formed into the same shape as said part of the stent tube whereby said part of the stent tube is not deformed by the inner catheter, wherein the inner catheter and stent tube are arranged such that the inner catheter can be pulled out of the stent tube.

2. A stent kit as claimed in claim 1, further comprising a straight cylindrical member in which said stent tube can be inserted.

3. A stent kit as claimed in claim 1, further comprising a pusher catheter located adjacent one of said first and second ends of said stent tube and aligned with the part of said stent tube at said one of said first and second ends, said inner catheter extending from within the pusher catheter into the stent tube, and further comprising coupling means for coupling said stent tube to said pusher catheter.

4. A stent kit as claimed in claim 3, further comprising a straight cylindrical member in which said stent tube can be inserted.

5. A stent kit comprising:
   a stent tube having first and second ends and having an arc-shaped part at least at one of said ends;
   an inner catheter fitting into said stent tube and having an arc-shaped part having the same shape as, and fitting within, said at least one arc-shaped part of said stent tube; and
   a pusher catheter located adjacent one of said first and second end of said stent tube and aligned with the portion of said stent tube at said one of said first and second ends, said inner catheter extending from within the pusher catheter into the stent tube, and further comprising coupling means for coupling said stent tube to said pusher catheter;
   wherein:
   said coupling means is composed of a filament extending through a radial opening formed in one of said pusher catheter and said stent tube, said filament having a knot tied therein, and a catching hole formed in a portion of a wall of the other of said stent tube and said pusher catheter at a location adjacent said one of said first and second ends of said stent tube; and
   wherein said knot fits loosely in said catching hole, and is supported, and prevented from moving inward through said catching hole, by said inner catheter while said inner catheter is located within said portion of a wall of said other of said stent tube and said pusher catheter.

6. A stent kit as claimed in claim 5, further comprising a straight cylindrical member in which said stent tube can be inserted.

7. A stent kit as claimed in claim 5, wherein said filament includes a distal portion extending beyond said catching hole and between said inner catheter and the wall of said other of said stent tube and said pusher catheter, when viewed from the side of said pusher catheter and stent tube.

8. A stent kit as claimed in claim 7, further comprising a straight cylindrical member in which said stent tube can be inserted.

* * * * *